Aug. 6, 1963 E. S. BOERNER Plant Pat. 2,273
CHRYSANTHEMUM PLANT
Filed Aug. 9, 1962
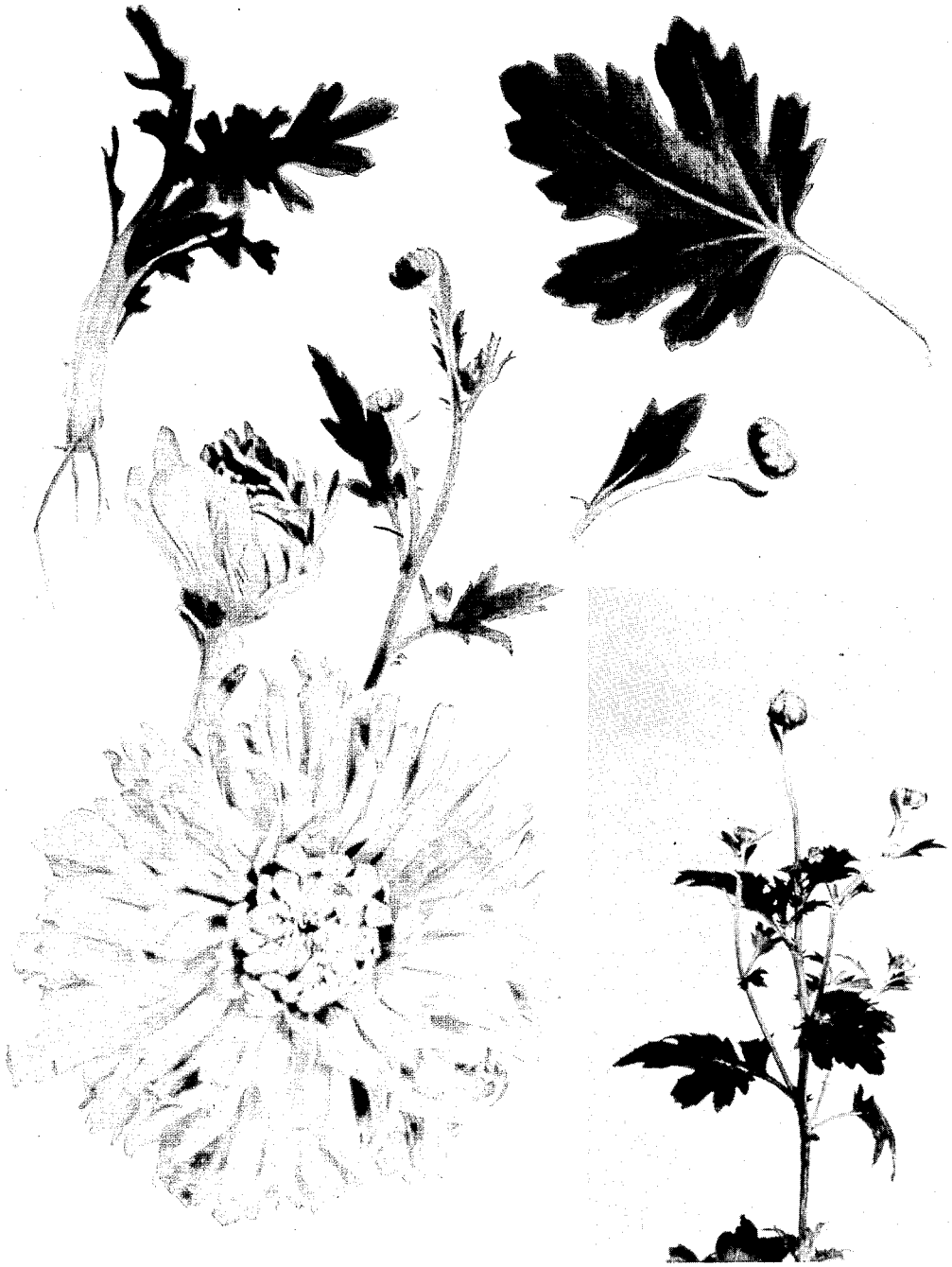
Inventor
E. S. Boerner
By: Robb & Robb
Attorneys.

United States Patent Office

Plant Pat. 2,273
Patented Aug. 6, 1963

2,273
CHRYSANTHEMUM PLANT

Eugene S. Boerner, Newark, N.Y., assignor to Jackson & Perkins Company, Newark, N.Y., a corporation of New York Filed Aug. 9, 1962, Ser. No. 216,007
1 Claim. (Cl. Plt.—82)

The present invention relates to a new and distinct variety of chrysanthemum plant of the incurved class, which was originated by me by crossing an unnamed and unpatented seedling derived from a cross of "Meadowlark" (Plant Patent No. 1,305) × "Thrush" (Plant Patent No. 1,168) with an unnamed and unpatented large-flowered Hortorum seedling.

The primary objective of this breeding was to produce a new chrysanthemum variety in which there is combined the strength and vigor of the unnamed parent seedling of "Meadowlark" × "Thrush" with the large flower size of the unnamed Hortorum seedling parent. This objective was fully achieved, along with other desirable improvements, as evidenced by the following unique combination of characteristics which are outstanding in the new variety and which distinguish it from its parents, as well as from all other varieties of which I am aware:

(1) A strong and vigorous habit of growth;
(2) Large flower size;
(3) An incurved and double flower form;
(4) Slightly notched petal tips; and
(5) A distinctive and attractive general color tonality of the flowers corresponding to Scarlet-Red, with the edges of the petals lightly overcast with Scarlet.

Asexual reproduction of the new variety by both top cuttings and underground runners, as performed outdoors at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, in the early morning during the latter part of the month of October:

Parentage: Seedling.
*Seed parent.*—An unnamed seedling of "Meadowlark" × "Thrush."
*Pollen parent.*—An unnamed large-flowered Hortorum seedling.

Classification: Incurved.
Growth: Free; attains height of about 22 inches.
Cold resistance: Hardy in northern New York State.
Blooming period: From early October until severe frost.

*Flower*

Bud:
*Color.*—When sepals first divide—Dragon's-Blood Red, Plate 13. When petals begin to unfurl—Jasper Red, Plate 13. When half-blown: inside—Scarlet-Red, Plate 1, lightly overcast with Jasper Red, Plate 13; outside—Light Coral Red, Plate 13, lightly overcast with Jasper Red, Plate 13.
*Peduncle.* — Color — Turtle Green, Plate 32. Strength—strong.

Bloom:
*Size.*—From 5½ inches to 6 inches.
*Stem.*—Strong.
*Form.*—Incurved.
*Petalage.*—Double.
*Color.*—Center of flower—Deep Chrome, Plate 3, lightly overcast with Ochraceous-Salmon, Plate 15. Outer petals—Scarlet, Plate 1, very lightly overcast with Grenadine, Plate 2. Base of petals—Pale Greenish-Yellow, Plate 5. Inside of petals—Scarlet-Red, Plate 1, with edges lightly overcast with Scarlet, Plate 1. Reverse of petals—Strawberry Pink, Plate 1, lightly overcast with Orient Pink, Plate 2.
*Petals.*—Texture—thin; crisp. Form—long oval; tips of petals slightly notched.
*Fragrance.*—Characteristic chrysanthemum.

*Plant*

Form: Upright.
Growth: Free.
Foliage:
*Size.*—Medium.
*Quantity.*—Normal.
*Color.*—Upper side—Dark Cress Green, Plate 31. Reverse side—Bice Green, Plate 17.
*Texture.*—Leathery.

I claim:

A new and distinct variety of chrysanthemum plant of the incurved class, substantially as herein shown and described, characterized particularly as to novelty by the unique combination of a strong and vigorous habit of growth, large flower size, an incurved and double form of the flowers, with the tips of the flower petals being slightly notched, and a distinctive and attractive general color tonality of the flowers corresponding to Scarlet-Red, with the edges of the petals lightly overcast with Scarlet.

No references cited.